(12) United States Patent
Robinson

(10) Patent No.: US 10,405,894 B2
(45) Date of Patent: Sep. 10, 2019

(54) CERVICAL MINIMAL ACCESS FUSION SYSTEM

(71) Applicant: SPECTRUM SPINE IP HOLDINGS, LLC, Atlanta, GA (US)

(72) Inventor: James C Robinson, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 19 days.

(21) Appl. No.: 15/116,789

(22) PCT Filed: Feb. 17, 2015

(86) PCT No.: PCT/US2015/016222
§ 371 (c)(1),
(2) Date: Aug. 4, 2016

(87) PCT Pub. No.: WO2015/123693
PCT Pub. Date: Aug. 20, 2015

(65) Prior Publication Data
US 2016/0346013 A1  Dec. 1, 2016

Related U.S. Application Data

(60) Provisional application No. 61/940,047, filed on Feb. 14, 2014.

(51) Int. Cl.
*A61B 17/70* (2006.01)
*A61B 17/80* (2006.01)
(Continued)

(52) U.S. Cl.
CPC ...... *A61B 17/7059* (2013.01); *A61B 17/7064* (2013.01); *A61B 17/8023* (2013.01);
(Continued)

(58) Field of Classification Search
CPC ........ A61B 17/7061–17/7064; A61B 17/7065; A61B 17/7058; A61B 17/8004;
(Continued)

(56) References Cited

U.S. PATENT DOCUMENTS 7,588,592 B2 * 9/2009 Winslow ............ A61B 17/7062
606/249
7,635,367 B2  12/2009 Groiso
(Continued)

OTHER PUBLICATIONS

European Search Report, EP-15748784.4, dated Sep. 13, 2017.

*Primary Examiner* — Jacqueline T Johanas
(74) *Attorney, Agent, or Firm* — FisherBroyles LLP; Anthony Dovale

(57) ABSTRACT

A cervical minimal access fusion system is presented. The system has a plate with a longitudinal axis and defining at least two bone screw bores therethrough and an intervertebral cage configured to be positioned between two adjacent cervical vertebrae. A method for a cervical minimal access fusion system is also presented. In one aspect, the method comprises the steps of accessing the facet joints of two adjacent cervical vertebrae, distracting the joints so as to increase the space between the two adjacent cervical vertebrae, placing an implant or structural bone graft in the space between the two adjacent cervical vertebrae to maintain the distraction, and compressing the two lateral masses to induce lordosis around the facet joint.

10 Claims, 9 Drawing Sheets

(51) Int. Cl.
*A61F 2/44* (2006.01)
*A61F 2/28* (2006.01)
*A61B 17/00* (2006.01)
*A61B 17/56* (2006.01)
*A61F 2/30* (2006.01)

(52) U.S. Cl.
CPC ........ *A61B 17/8085* (2013.01); *A61F 2/2846* (2013.01); *A61F 2/4455* (2013.01); *A61B 2017/00004* (2013.01); *A61B 2017/00946* (2013.01); *A61B 2017/564* (2013.01); *A61F 2002/30622* (2013.01)

(58) Field of Classification Search
CPC ............ A61B 17/8023; A61B 17/7059; A61B 2017/681; A61B 17/7062; A61B 17/8085
See application file for complete search history.

(56) References Cited

U.S. PATENT DOCUMENTS

| | | | |
|---|---|---|---|
| 7,824,431 B2 | 11/2010 | McCormack | |
| 8,211,109 B2 | 7/2012 | Groiso | |
| 8,348,979 B2 | 1/2013 | McCormack | |
| 8,372,075 B2 | 2/2013 | Groiso | |
| 9,480,513 B2 * | 11/2016 | Waizenegger | A61B 17/68 |
| 9,918,762 B2 * | 3/2018 | Federspiel | A61B 17/8085 |
| 2002/0013586 A1 * | 1/2002 | Justis | A61B 17/7011 |
| | | | 606/255 |
| 2003/0074001 A1 * | 4/2003 | Apfelbaum | A61B 17/80 |
| | | | 606/71 |
| 2004/0102777 A1 * | 5/2004 | Huebner | A61B 17/1728 |
| | | | 606/281 |
| 2005/0070900 A1 * | 3/2005 | Serhan | A61B 17/3468 |
| | | | 623/17.12 |
| 2006/0235398 A1 * | 10/2006 | Farris | A61B 17/8009 |
| | | | 606/71 |
| 2007/0299442 A1 * | 12/2007 | Eisermann | A61B 17/7007 |
| | | | 606/86 A |
| 2008/0154374 A1 * | 6/2008 | Labrom | A61F 2/4405 |
| | | | 623/17.12 |
| 2008/0161929 A1 | 7/2008 | McCormack et al. | |
| 2009/0312763 A1 * | 12/2009 | McCormack | A61B 17/025 |
| | | | 606/83 |
| 2010/0004687 A1 * | 1/2010 | Falahee | A61F 2/4405 |
| | | | 606/246 |
| 2010/0087822 A1 | 4/2010 | Groiso | |
| 2010/0145386 A1 * | 6/2010 | Greenhalgh | A61B 17/7059 |
| | | | 606/246 |
| 2010/0191241 A1 * | 7/2010 | McCormack | A61B 17/025 |
| | | | 606/83 |
| 2010/0228291 A1 * | 9/2010 | Butler | A61B 17/7059 |
| | | | 606/259 |
| 2011/0009968 A1 | 1/2011 | McCormack | |
| 2011/0060372 A1 * | 3/2011 | Allison | A61B 17/8019 |
| | | | 606/286 |
| 2012/0158066 A1 * | 6/2012 | Freese | A61B 17/7059 |
| | | | 606/279 |
| 2012/0277801 A1 * | 11/2012 | Marik | A61B 17/7064 |
| | | | 606/279 |
| 2014/0018855 A1 * | 1/2014 | Stern | A61B 17/7059 |
| | | | 606/246 |
| 2014/0046445 A1 * | 2/2014 | Brennan | A61F 2/4455 |
| | | | 623/17.16 |
| 2014/0046447 A1 | 2/2014 | Dunworth et al. | |
| 2014/0207197 A1 * | 7/2014 | Reisberg | A61B 17/823 |
| | | | 606/324 |
| 2014/0336768 A1 * | 11/2014 | Blain | A61B 17/7059 |
| | | | 623/17.16 |
| 2014/0350601 A1 * | 11/2014 | Altarac | A61B 17/7059 |
| | | | 606/246 |
| 2014/0379034 A1 * | 12/2014 | Stern | A61B 17/7059 |
| | | | 606/279 |
| 2015/0088206 A1 * | 3/2015 | Bullard | A61B 17/8023 |
| | | | 606/279 |

* cited by examiner

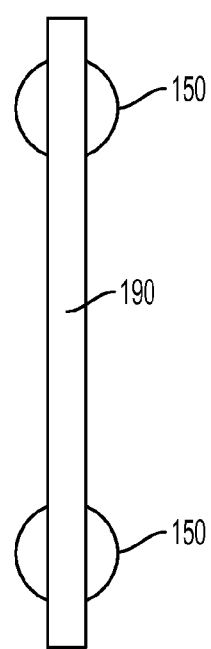 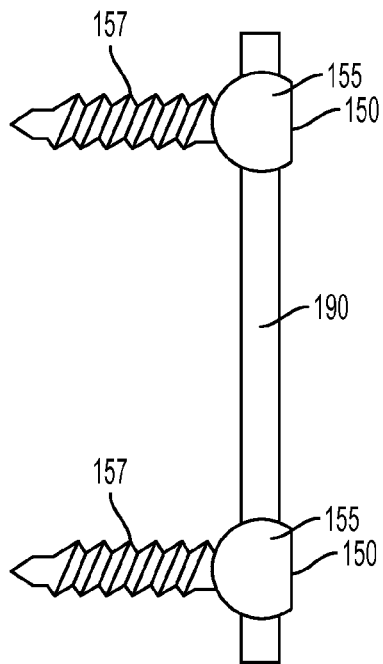
FIG. 10A  FIG. 10B
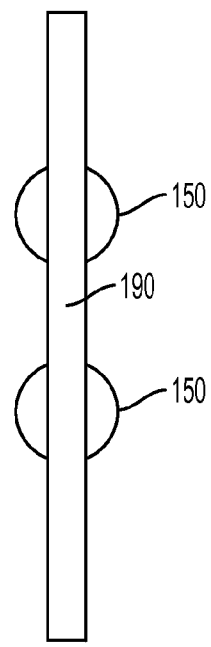 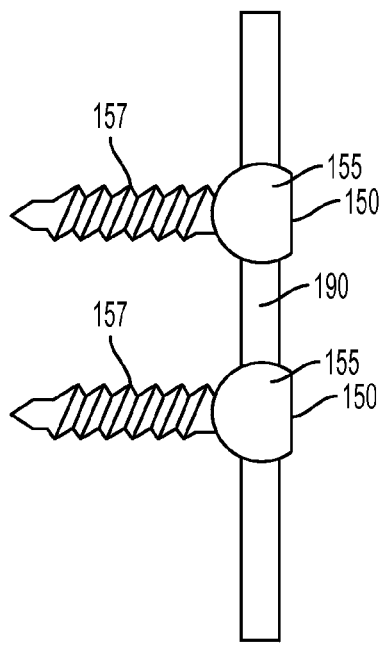
FIG. 11A  FIG. 11B

CERVICAL MINIMAL ACCESS FUSION SYSTEM

CROSS REFERENCE TO RELATED APPLICATIONS

This application claims the benefit of and priority to U.S. Provisional Patent Application No. 61/940,047, entitled CERVICAL MINIMAL ACCESS FUSION SYSTEM, filed Feb. 14, 2014, which is incorporated in its entirety in this document by reference.

FIELD OF THE INVENTION

This invention relates generally to spinal surgery, and more particularly to devices and methods of stabilization of the cervical spine by inserting an implant configured to increase disk space and lordosis in the cervical spine.

BACKGROUND OF THE INVENTION

Cervical spine surgery is generally performed on an elective basis to treat either spinal cord impingement or spinal instability. Spinal cord impingement generally requires decompression surgery. Spinal instability generally requires fusion surgery. The two procedures are often combined, as a decompression may de-stabilize the spine and create the need for a fusion to add stability.

The cervical spine can either be approached from the front (anterior approach) or from the back (posterior approach). In general, where possible, most surgeons favor an anterior approach for most conditions. An anterior approach generally results in less disruption of the normal musculature and is also easier to maintain the normal alignment of the spine. However, a posterior approach may have the benefit of making it easier to restore lordosis.

SUMMARY

Presented herein is a minimal access fusion system for the cervical spine. The system comprises a plate having a longitudinal axis and defining at least two bone screw bores therethrough. The system also comprises an inter-vertebral cage configured to be positioned between two adjacent cervical vertebrae. The plate is configured to change in longitudinal length and can be inserted in a first position, where the longitudinal length is substantially at its longest, and moved to a second position, where the longitudinal length is shorter. In use, when the plate is shortened after insertion, the cage, which is already positioned between two adjacent cervical vertebrae, acts as a fulcrum point, raising the intervertebral space between the anterior portion of the vertebrae.

A method for a cervical minimal access fusion system is also presented. In one aspect, the method comprises the steps of accessing the facet joints of two adjacent cervical vertebrae, distracting the joints so as to increase the space between the two adjacent cervical vertebrae, placing an implant or structural bone graft in the space between the two adjacent cervical vertebrae to maintain the distraction, and compressing the two lateral masses to induce lordosis across the motion segment.

Related methods of operation are also provided. Other apparatuses, methods, systems, features, and advantages of the cervical minimal access fusion system and the method of its use will be or become apparent to one with skill in the art upon examination of the following figures and detailed description. It is intended that all such additional apparatuses, methods, systems, features, and advantages be included within this description, be within the scope of the cervical minimal access fusion system and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 10A is a top plan view of one aspect of a cervical fusion system having a connecting bar, in a first, starting, position;

FIG. 10B is a side view of the cervical fusion system of FIG. 10A;

FIG. 11A is a top plan view of the cervical fusion system of FIG. 10A in a second, compressed, position;

FIG. 11B is a side view of the cervical fusion system of FIG. 11A; and

DESCRIPTION OF THE INVENTION

Figure 1:
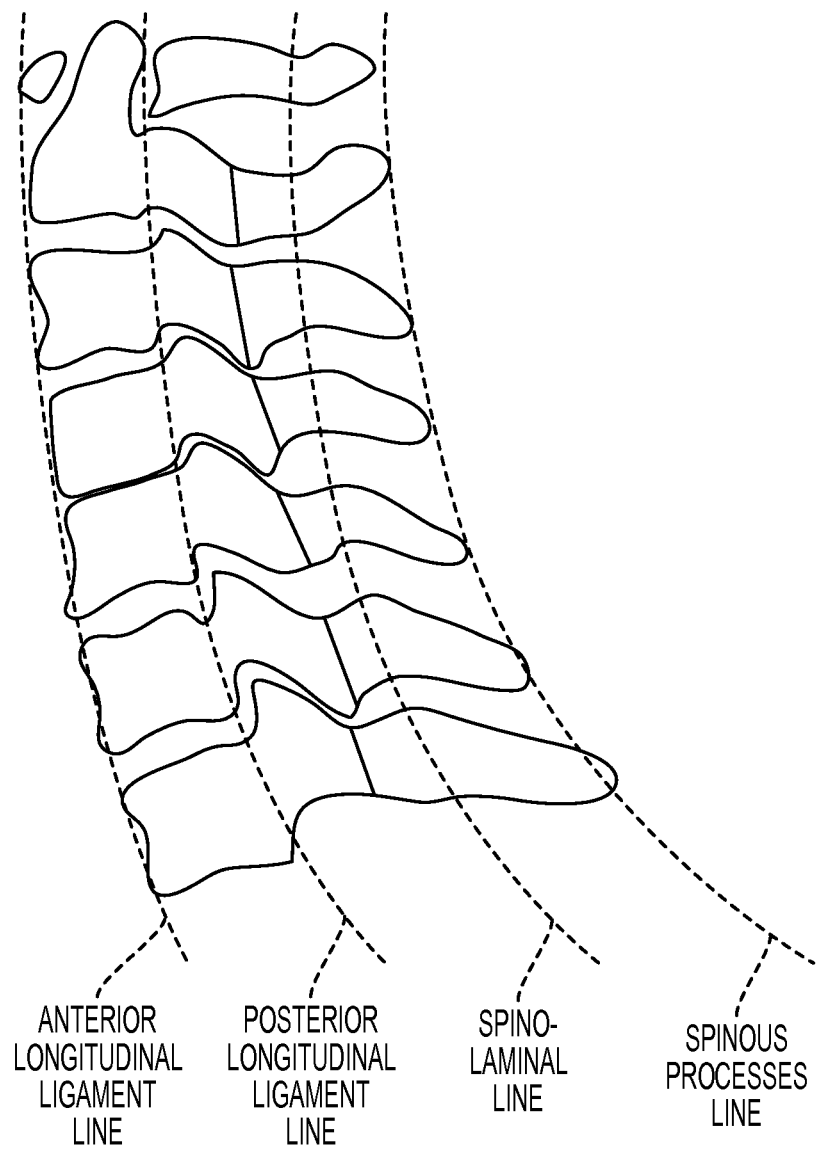
FIG. 1 is a side view of a cervical spine showing two adjacent vertebrae having minimal intervertebral spacing.
Figure 2:
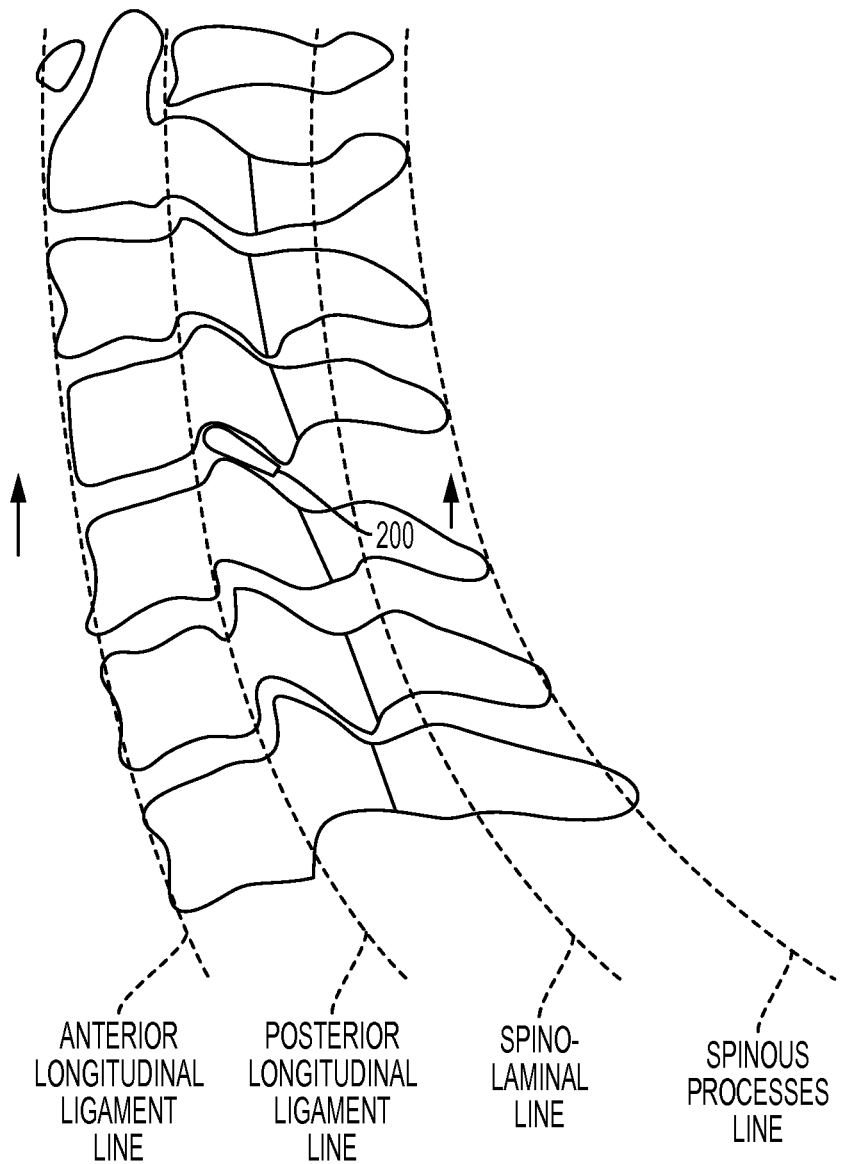
FIG. 2 is a side view of the cervical spine of FIG. 1, showing an intervertebral cage positioned therebetween the two adjacent vertebrae.
Figure 3:
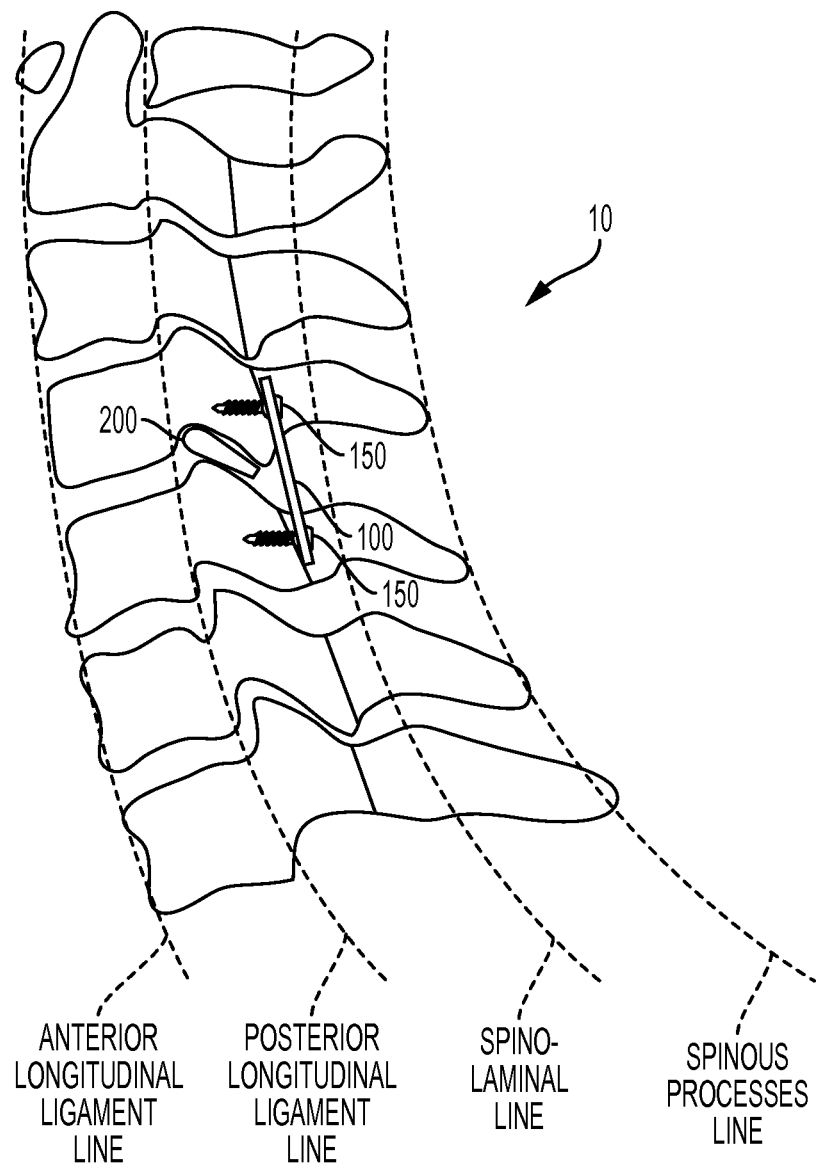
FIG. 3 is a side view of the cervical spine of FIG. 1, showing the intervertebral cage of FIG. 2 and a cervical plate fastened into each of the adjacent vertebrae.
Figure 4:
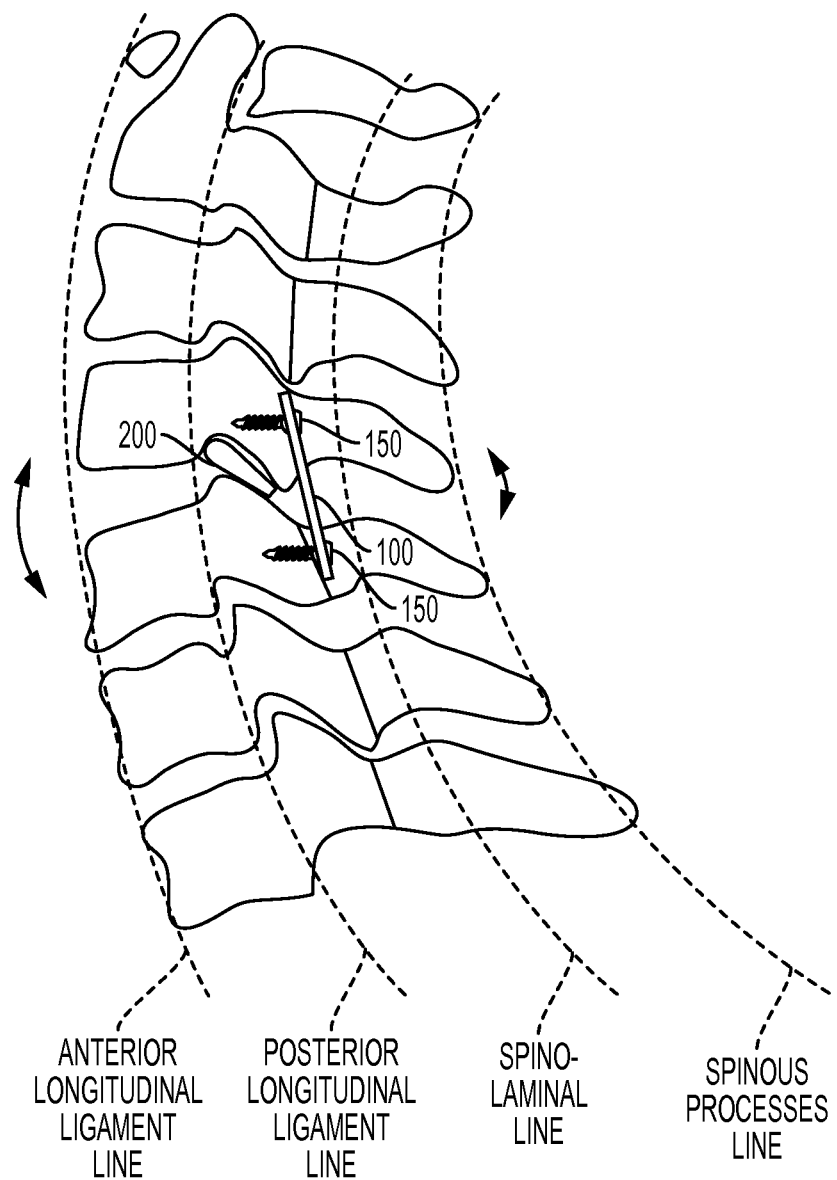
FIG. 4 is a side view of the cervical spine of FIG. 1, showing the intervertebral cage of FIG. 2 and the cervical plate of FIG. 3, where the plate is positioned from a first position to a second position where the bone screws are compressed toward one another.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

The term "substantially," as used herein, may be applied to modify any quantitative representation which could permissibly vary without resulting in a change in the basic function to which it is related.

In one aspect, presented herein is a minimal access fusion system 10 for the cervical spine. The system 10 comprises a plate 100 having a longitudinal axis $A_L$ and defining at least two bone screw bores 120 therethrough. The system further comprises an inter-vertebral cage 200 configured to be positioned between two adjacent cervical vertebrae. The cage 200 can be positioned anteriorly-posteriorly within the facet joint.

In one aspect, the cage 200 is positioned from a posterior aspect. The cage 200 can define at least one graft window 210, but does not necessarily have to. Many shapes and sizes of cages are contemplated within the system.

In yet another aspect, the plate 100 is configured to change in longitudinal length 110. In this way, the plate can be inserted in a first position, where the longitudinal length 110 is substantially at its longest, and moved to a second position, where the longitudinal length is shorter. That is, the plate 100 can be selectively adjustable by a user about and between the first position, in which the longitudinal length is a first distance, and the second position in which the longitudinal length 110 is a second distance that is less than the first distance. In use, when the plate is shortened after insertion, the cage 200, which can already be positioned between two adjacent cervical vertebrae, acts as a fulcrum point, thereby raising the intervertebral space between the anterior portions of the vertebrae. Alternatively, in one aspect and as described more fully below, the longitudinal length of the plate 100 can remain fixed, while a longitudinal distance between a portion of at least two bone screws 150 can be selectively adjustable by a user about and between a first distance and a second distance that is less than the first distance.

In one exemplified aspect, the plate 100 defines at least one bone screw bore 120 substantially adjacent the distal end 140 of the plate and at least one bone screw bore 120 positioned substantially adjacent the proximal end 130 of the plate. In another aspect, a first bone screw 150 would be inserted through the distal bone screw bore and into a first cervical vertebra when the plate is in the first position. Then, a second bone screw 150 would be inserted through the proximal bone screw bore and into a second cervical vertebra, also when the plate is in the first position. Then, the plate would be moved to the second position, substantially bringing the bone screws closer together and raising the anterior portion of the vertebrae.

Figure 5A:
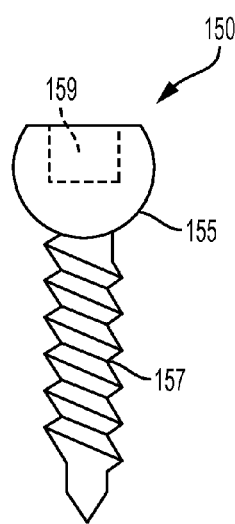
FIG. 5A is a side view of a polyaxial bone screw for use in a cervical fusion system.
Figure 5B:
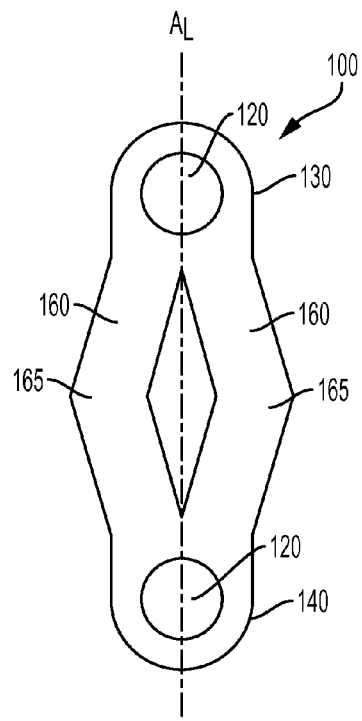
FIG. 5B is a top plan view of one aspect of a cervical access fusion system in a first, starting, position.
Figure 5C:
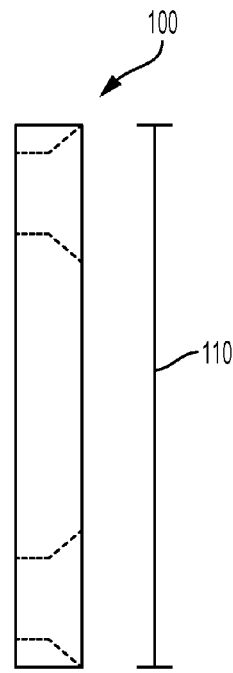
FIG. 5C is a side view of the cervical access fusion system of FIG. 5B.
Figure 6:
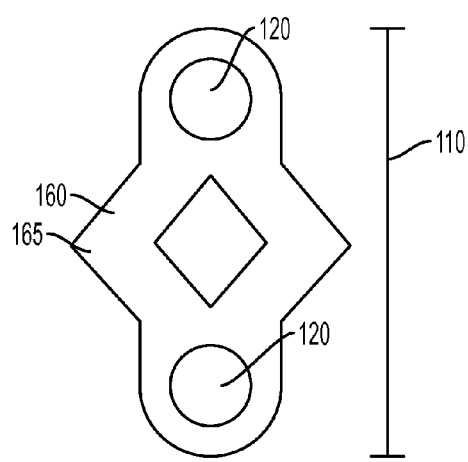
FIG. 6 is a top plan view of the cervical fusion system of FIG. 5B in a second, compressed, position.
Figure 7A:
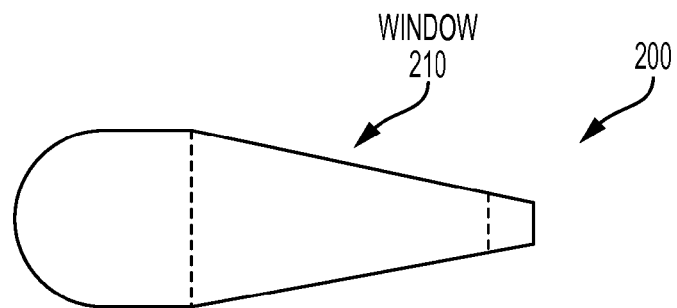
FIG. 7A is a side view of one aspect of an intervertebral cage device having a graft widow.
Figure 7B:
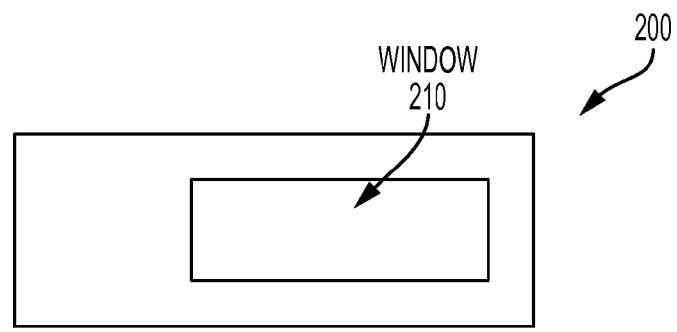
FIG. 7B is a top plan view of the intervertebral cage device of FIG. 7A.
Figure 7C:
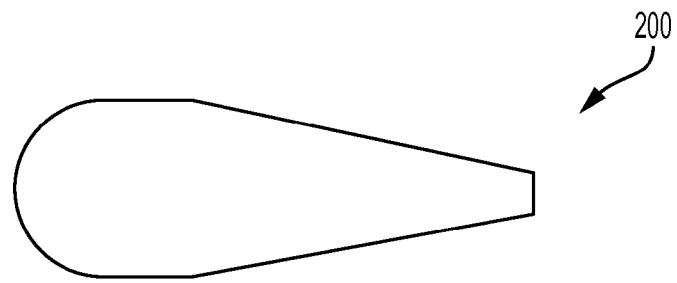
FIG. 7C is a side view of one aspect of an intervertebral cage device without a graft window.

As can be seen in FIG. 5B, the plate 100 can comprise a pair of legs 160, each having an elbow 165 slightly bent outwardly creating a space therebetween. In this aspect, when the plate is compressed longitudinally (as the plate is adjusted from the first position towards the second position), each of the legs bend outwardly, as shown in FIG. 6, increasing the space between the elbows 165.

The plate 100 can comprise a sufficiently malleable material that also retains its shape once compressed. That is, as the plate is moved from the first position to the second position, the plate 100 can be formed from a material that can retain its shape in the second position. For example, the plate can comprise, a biocompatible material such as stainless steel alloy or a titanium alloy such as TA6V of medical grade having suitable elasticity and mechanical strength.

Figure 8A:
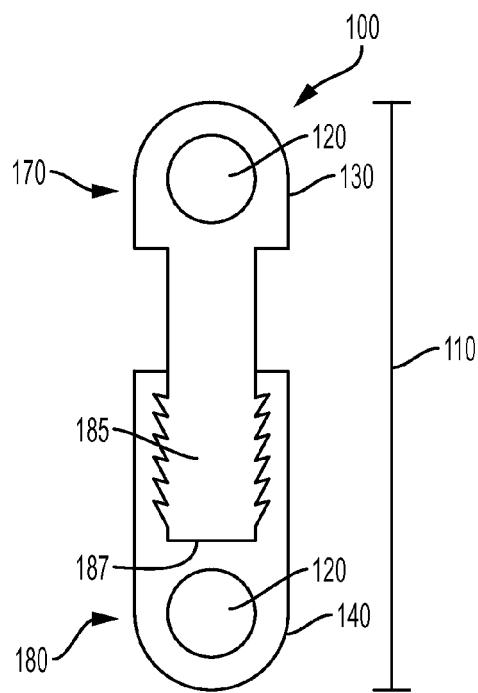
FIG. 8A is a top plan view of one aspect of a cervical access fusion system in a first, starting, position.
Figure 8B:
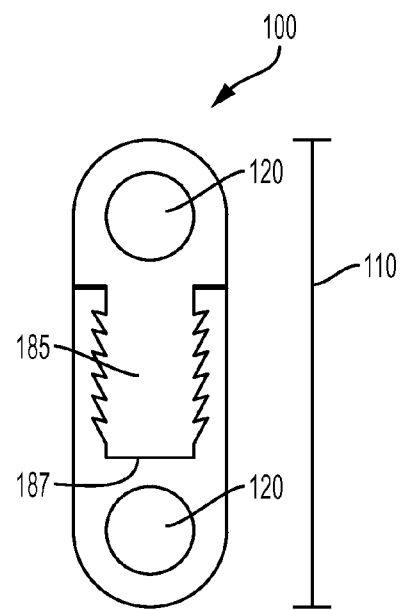
FIG. 8B is a top plan view of the cervical fusion system of FIG. 8A in a second, compressed, position

In yet another aspect, as seen in FIG. 8, the plate 100 can comprise an upper portion 170 and a separate lower portion 180, wherein one of the portions has a ribbed tab 185 and the other portion has a complementary slot 187 for receiving at least a portion of the tab therein. In this aspect, when the tab is pulled through the slot, the tab acts to ratchet the upper portion closer to the lower portion. That is, at least a portion of the tab is insertable into the slot, and the ribs of the tab can prevent or restrict the tab from exiting the slot. In use, the distance between the proximal end 130 of the upper portion 170 and the distal end 140 of the lower portion 180 can be selectively adjusted by the user. Once selected, the ribs of the tab can securely couple the upper and lower portions of the plate together so that the longitudinal length 110 of the plate cannot inadvertently increase.

Figure 9:
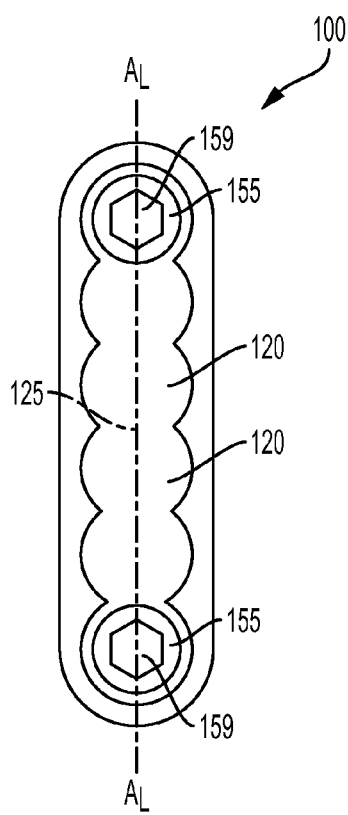
FIG. 9 is a top plan view of one aspect of a cervical fusion system in a first, starting, position.

Additionally, the plate 100 can also define a series of connected screw bores 120, as shown in FIG. 9. The series of connected bone screw bores can be defined such that each bore 120 connects at a narrow 125. In this aspect, the head 155 of the bone screw 150 can define a tool aperture 159 that is keyed to accept the distal end of a tool. In use, a first bone screw can be completely secured to a first vertebra, thereby securing a first portion of the plate 100 to the first vertebra. A second bone screw 150 can be partially secured to the second vertebra, allowing longitudinal movement of the screw with respect to the plate. Then, the tool can be used to compress or urge the heads of the first and second bone screws closer to each other (decreasing the longitudinal distance between the heads of the first and second bone screws) prior to fully securing the second bone screw 150, which locks the second bone screw into position relative to the plate 100. In this aspect, it may be beneficial for a portion of a shank 157 of a bone screw proximate the head 155 of the bone screw to be greater in diameter than the remaining portion of the shank. Specifically, the diameter of the bone screw 150 proximate the head of the bone screw can be larger than a narrow 125. As such, when the bone screw is driven into the specified vertebral bone sufficiently, the screw can be retained within the bone screw bore 120 and can restrict or prevent the plate from moving longitudinally with respect to the screw.

In still another aspect, the cervical minimal access fusion system 10 comprises at least two bone screws 150 and a connecting rod 190 engageable with a portion of each of the bone screws such that the connecting rod extends therebetween the bone screws, as illustrated in FIGS. 10-11. In this aspect, the bone screws 150 can be inserted into position with the connecting rod 190 substantially loosely engaged with one or both of the screws. Then, the heads 155 of the bone screws 150 can be compressed or urged longitudinally toward one another and locked into place by tightening the rod onto a portion of each of the bone screws. It is contemplated that conventional bone screw-connecting rod configurations can be employed.

Figure 12:
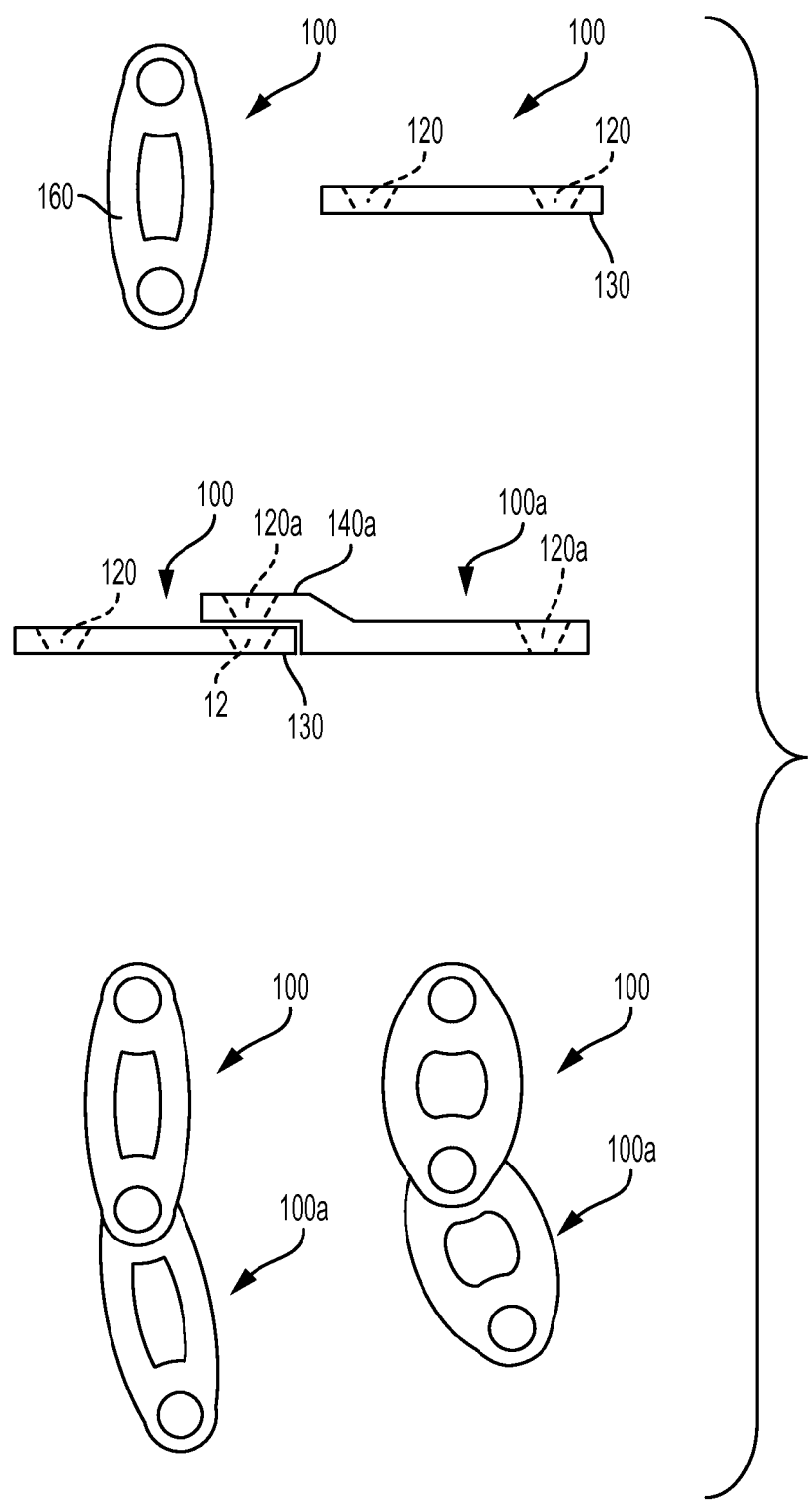
FIG. 12 is a series of views of one aspect of a cervical fusion system comprising a plurality of plates configured to be used in a multi-level fusion surgery.

In one exemplified aspect, the cervical minimal access fusion system 10 comprises a plurality of plates configured to be used in a multi-level fusion surgery, as shown in FIG. 12. In this aspect, the system comprises a first plate 100 and at least one connector plate 100a having a raised distal end 140a configured to overlie the proximal end 130 of the first plate 100. The remainder of the connector plate 100a can remain substantially coplanar with the first plate 100. The connector plate 100a can otherwise be configured similar to the plates 100 described herein. In this aspect, a proximal end 130 of the first plate 100 can underlie the distal end 140a of the connector plate such that the bone screw bore 120 on the proximal end 130 of the first plate 100 is substantially concentric with the bone screw bore 120a of the distal end 140a of the connector plate 100a. In this manner, a single bone screw can be used in the concentric bores, both fastening the first plate and the connector plate to a vertebra and connecting the two plates. In yet another aspect, the distal end of the connector plate 100a can be registered with the proximal end of the first plate 100 to restrict rotation of one plate with respect to the other. Standard star-burst registration of something similar can be used.

In this aspect, the cervical minimal access fusion system 10 of FIG. 12 can be used to raise the intervertebral space between the anterior portion of three or more adjacent vertebrae. For example, the first plate 100 can be attached to a first and second vertebrae. The first plate can be compressed longitudinally to a desired length to raise the space between the anterior portion of the first and second vertebrae. The connector plate 100a can be positioned over a portion of the first plate and attached to the second vertebra and a third vertebra. The second plate can then be compressed longitudinally to a desired length to raise the space between the anterior portion of the second and third vertebrae. As can be appreciated, any number of plates can be coupled together like this to increase the anterior space between any number of adjacent vertebra.

A method for a cervical minimal access fusion system is also presented. In one aspect, the method comprises the steps of accessing the facet joints of two adjacent cervical vertebrae, distracting the joints so as to increase the space between the two adjacent cervical vertebrae, placing an implant or structural bone graft in the space between the two adjacent cervical vertebrae to maintain the distraction, and compressing the two lateral masses to induce lordosis around the facet joint.

In one aspect, the method comprises placing a cervical plate 100, as described herein above, longitudinally connected to each of the two at least one of the lateral masses of each of the two adjacent cervical vertebrae. A first bone screw 150 can be positioned through a portion of the distal end 140 of the plate and a second bone screw can be positioned through a portion of the proximal end 130 of the plate. In this aspect, the step of compressing the two lateral masses to induce lordosis or on the facet joint comprises moving the bone screws closer to one another along the longitudinal axis of the plate. Once the correct amount of lordosis is achieved, the bone screws can be fixed positionally to maintain the compression.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A cervical minimal access fusion system for a cervical spine comprising:

a plate having a longitudinal axis and defining at least two bone screw bores therethrough, wherein the plate has a longitudinal length, and wherein the plate comprises a pliable material to enable it to be selectively adjustable about and between a first position, in which the longitudinal length is a first distance, and a second position in which the longitudinal length is a second distance that is less than the first distance, wherein the pliable material is sufficiently and uniformly stiff to maintain the plate in the second position;

a plurality of bone screws, wherein at least one bone screw of the plurality of bone screws is configured to extend through a first bone screw bore of the plate and into a first vertebra, and wherein at least one other bone screw of the plurality of bone screws is configured to extend through a second bone screw bore of the plate and into a second, adjacent vertebra; and an intervertebral cage configured to be positioned between the first vertebra and the second, adjacent vertebra and configured to act as a fulcrum point, wherein said plate is configured to adjust from the first distance to the second distance after insertion into said cervical spine bringing the at least one bone screw and the at least one other bone screw closer together and, with the intervertebral cage, when positioned between the first vertebra and the adjacent second vertebra, configured to act as said fulcrum point, thereby raising the intervertebral space between an anterior portion of the first vertebra and the adjacent second vertebra of the cervical spine.

2. The system of claim 1, wherein the intervertebral cage is positionable anteriorly-posteriorly within a facet joint between the first and second vertebrae.

3. The system of claim 1, wherein the intervertebral cage defines at least one graft window.

4. The system of claim 1, wherein the plate is formed from a biocompatible material.

5. The system of claim 1, wherein the plate comprises a pair of legs, wherein each leg has an elbow bent outwardly creating a space therebetween the pair of legs, and wherein as the plate is adjusted from the first position towards the second position, each leg of the pair of legs bends outwardly, thereby increasing the space between the elbows.

6. A cervical minimal access fusion system for increasing disk space and lordosis between a first vertebra and an adjacent second vertebra in a cervical spine comprising:
   a first plate having a proximal end and an opposed distal end, wherein a first bone screw bore is defined in the proximal end and a second bone screw bore is defined the distal end of the first plate;
   at least one connector plate having a proximal end and an opposed, raised distal end, wherein a first connector plate bone screw bore is defined in the proximal end and a second connector plate bone screw bore is defined in the distal end of the connector plate, wherein the raised distal end of the connector plate is configured to overlie the proximal end of the first plate such that the first bone screw bore on the proximal end of the first plate is substantially concentric with the second connector plate bone screw bore of the distal end of the connector plate; and
   at least three bone screws, wherein a first bone screw is configured to extend through the second bone screw bore of the distal end of the first plate and into a first vertebra, wherein a second bone screw is configured to extend through both the first bone screw bore of the proximal end of the first plate and the second connector plate bone screw bore of the distal end of the connector plate and into a second vertebra, and wherein a third bone screw is configured to extend through the first connector plate bone screw bore of the proximal end of the connector plate and into a third vertebra; and
   an intervertebral cage configured to be positioned between the first vertebra and the adjacent second vertebra and act as a fulcrum point,
   wherein each of the first plate and the connector plate has a longitudinal length and comprises a pliable material to enable it to be selectively adjustable about and between a first position, in which the longitudinal length of each plate is a first distance, and a second position in which the longitudinal length of each plate is a second distance that is less than the first distance, wherein the pliable material is sufficiently and uniformly stiff to maintain the plate in the second position to increase lordosis in the cervical spine.

7. The system of claim 6, wherein the intervertebral cage is positionable anteriorly-posteriorly within the facet joint between the first and second vertebrae and configured to raise the intervertebral space between an anterior portion of the first vertebra and the adjacent second vertebra of the cervical spine.

8. A method for stabilization of the cervical spine by inserting an implant configured to increase disk space and lordosis between a first and second vertebra in the cervical spine comprising:
   providing a cervical plate having a longitudinal axis and defining at least two bone screw bores therethrough, wherein the plate has a longitudinal length and comprises a pliable material to enable it to be selectively adjustable about and between a first position, in which the longitudinal length is a first distance, and a second position in which the longitudinal length is a second distance that is less than the first distance, wherein the pliable material is sufficiently and uniformly stiff to maintain the plate in the second position;
   inserting a first bone screw through a first bone screw bore of the plate and into a posterior portion of the first vertebra;
   inserting a second bone screw through a second bone screw bore of the plate and into a posterior portion of the second vertebra;
   compressing a head of at least one of the first and second bone screw toward a head of the other bone screw; and
   positionally fixing the bone screws to maintain the compression.

9. The method of claim 8, further comprising positioning an intervertebral cage between the first vertebra and the second vertebra prior to the compressing to act as a fulcrum point.

10. The method of claim 9, wherein the intervertebral cage is positioned anteriorly-posteriorly within a facet joint between the first and second vertebrae to raise the intervertebral space between an anterior portion of the first vertebra and the adjacent second vertebra of the cervical spine.

* * * * *